US012687542B2

(12) United States Patent
Wang et al.

(10) Patent No.: US 12,687,542 B2
(45) Date of Patent: Jul. 21, 2026

(54) NANOFLOWER IMMUNOCHROMATOGRAPHIC STRIP FOR DETECTING HEAVY METAL MERCURY IONS AND USE THEREOF

(71) Applicant: Fujian Agriculture and Forestry University, Fuzhou (CN)

(72) Inventors: Shihua Wang, Fuzhou (CN); Mingke Dong, Fuzhou (CN); Sumei Ling, Fuzhou (CN); Rongzhi Wang, Fuzhou (CN); Kunzhi Jia, Fuzhou (CN); Jingjing Lin, Fuzhou (CN); Yang Xu, Fuzhou (CN); Aidi Xu, Fuzhou (CN); Menghao Wan, Fuzhou (CN)

(73) Assignee: Fujian Agriculture and Forestry University, Fuzhou (CN)

( * ) Notice: Subject to any disclaimer, the term of this patent is extended or adjusted under 35 U.S.C. 154(b) by 615 days.

(21) Appl. No.: 18/122,720

(22) Filed: Mar. 17, 2023

(65) Prior Publication Data

US 2023/0296599 A1    Sep. 21, 2023

(30) Foreign Application Priority Data

Mar. 18, 2022    (CN) .......................... 202210268690.3

(51) Int. Cl.
G01N 33/543 (2006.01)
C07K 16/44 (2006.01)
(Continued)

(52) U.S. Cl.
CPC ....... G01N 33/54388 (2021.08); C07K 16/44 (2013.01); G01N 33/532 (2013.01);
(Continued)

(58) Field of Classification Search
None
See application file for complete search history.

(56) References Cited

U.S. PATENT DOCUMENTS 5,532,136 A * 7/1996 Carlson ................. C07K 16/00
436/83
5,639,624 A * 6/1997 Wagner ................. G01N 33/84
435/7.1
(Continued)

FOREIGN PATENT DOCUMENTS

CN          101139398 A       3/2008
CN          101948807 A  *    1/2011
(Continued)

OTHER PUBLICATIONS

Translation of CN 103499688 B, Zhang, Hai-tang, Dec. 2, 2015 (Year: 2015).*

(Continued)

*Primary Examiner* — Henry H Nguyen
(74) *Attorney, Agent, or Firm* — Bayramoglu Law Offices LLC

(57) ABSTRACT

A nanoflower immunochromatographic strip for detecting heavy metal mercury ions is provided. The nanoflower immunochromatographic strip includes the following components: a plastic outer shell, a sample pad, an immunoprobe joint pad, a nitrocellulose membrane and an absorbent pad; the immunoprobe joint pad is dropwise added with a gold nano-immunoprobe labeled with an anti-mercury-ion monoclonal antibody; the anti-mercury-ion monoclonal antibody is a monoclonal antibody secreted by an anti-$Hg^{2+}$-ITCBE hapten murine hybridoma cell strain 7A1; and a preservation number of the murine hybridoma cell strain 7A1 is CGMCC No. 23879. The nanoflower immunochromatographic strip detects a heavy metal hapten $Hg^{2+}$-ITCBE, with a detection threshold of 50 ng/mL and a detection limit of 0.39 ng/mL, has strong specificity, high sensitivity, good repeatability and rapid detection, and is of great significance for monitoring residue of heavy metal mercury.

1 Claim, 9 Drawing Sheets

(51) Int. Cl.
    *G01N 33/532* (2006.01)
    *G01N 33/84* (2006.01)
(52) U.S. Cl.
    CPC ......... *G01N 33/84* (2013.01); *C07K 2317/33*
    (2013.01); *C07K 2317/92* (2013.01)

(56) References Cited

U.S. PATENT DOCUMENTS

| | | | | |
|---|---|---|---|---|
| 2007/0178544 | A1* | 8/2007 | Tamura | C07K 16/44 |
| | | | | 435/7.92 |
| 2015/0053868 | A1* | 2/2015 | Thalappil | G01N 21/643 |
| | | | | 252/301.4 F |
| 2017/0336398 | A1* | 11/2017 | Lin | G01N 33/581 |

FOREIGN PATENT DOCUMENTS

| | | | | | |
|---|---|---|---|---|---|
| CN | 103499688 | A | * | 1/2014 | ........... G01N 33/577 |
| CN | 112379088 | A | * | 2/2021 | ........... G01N 33/532 |

OTHER PUBLICATIONS

Translation of CN112379088A, Jia, Kun-zhi, Feb. 19, 2021 (Year: 2021).*
Translation of CN 101948807 A, Zhao, Li, Jan. 19, 2011 (Year: 2011).*
Yang Fengli, et al., Preparation and characterization of specific monoclonal antibodies of mercury, High Technology Letters, May 2008, pp. 531-536, vol. 18, No. 5.
Sumei Ling, et al., Development of sensitive and portable immunosensors based on signal amplification probes for monitoring the mercury (II) ions, Biosensors and Bioelectronics, 2022, pp. 1-6, vol. 217 No. 114676.

* cited by examiner

Lane 1: KLH Lane 2: Hg$^{2+}$-ITCBE-KLH Lane 3: Hg$^{2+}$-ITCBE-BSA Lane 4: BSA

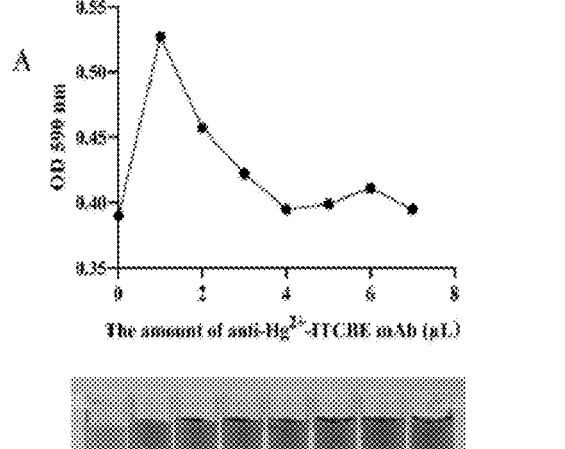
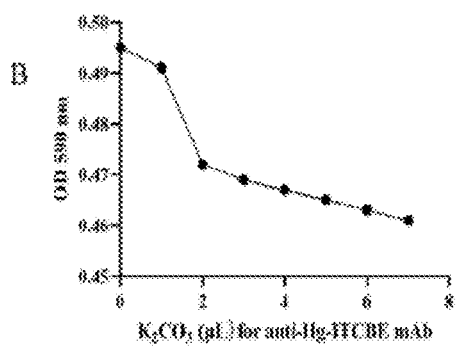
FIG. 11A　　　　　　　　　　　　　　FIG. 11B
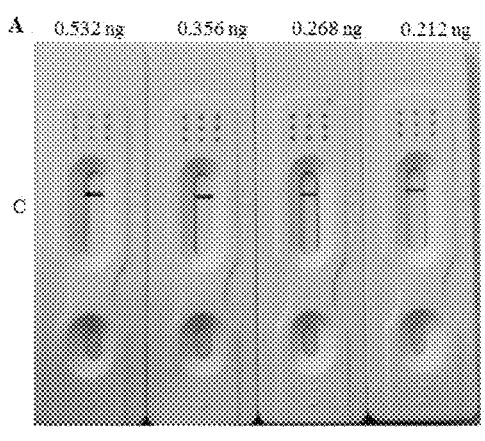
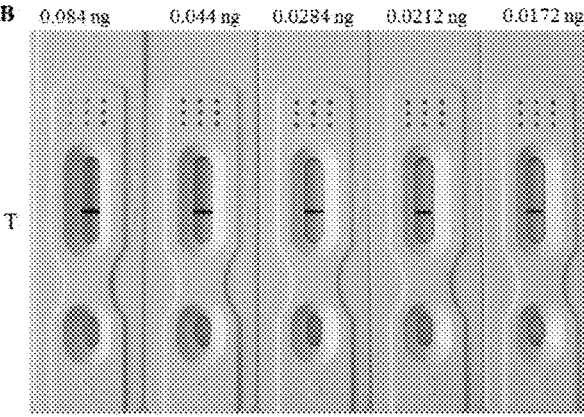
FIG. 12A　　　　　　　　　　　　　　FIG. 12B

A

B

NANOFLOWER IMMUNOCHROMATOGRAPHIC STRIP FOR DETECTING HEAVY METAL MERCURY IONS AND USE THEREOF

CROSS REFERENCE TO THE RELATED APPLICATIONS

This application is based upon and claims priority to Chinese Patent Application No. 202210268690.3, filed on Mar. 18, 2022, the entire contents of which are incorporated herein by reference.

TECHNICAL FIELD

The present invention belongs to the technical field of rapid detection of heavy metal pollution, and particularly relates to a nanoflower immunochromatographic strip for detecting heavy metal mercury ions and a use thereof.

BACKGROUND

With the continuous improvement of living standards in today's society, a large number of industrial pollutants and agricultural activities that have not been effectively treated result in excessive out-emission of heavy metals, which directly or indirectly endanger the environment and human health through atmospheric deposition, agricultural fertilization, human consumption and other ways. When discharged into the environment, heavy metals will quickly settle into sediments, which can easily cause secondary release, further polluting a water body and resulting in great harm to aquatic organisms such as fish. When polluted wastewater containing heavy metals is used to irrigate farmlands, it causes serious pollution to soil and crops. These heavy metal pollution will be enriched by hundreds or thousands of times by the biological amplification of a food chain, and eventually enter human organs to accumulate, resulting in a huge threat to human health. Plants have the ability to absorb and accumulate mercury, and absorb and accumulate more mercury with the increase of mercury content in water and soil. Mercury in the plants can be used as animal feed and cyclically enters into animal bodies. Traditional detection methods for mercury and other heavy metals, such as Atomic Absorption Spectrometry, Inductively Coupled Plasma Mass Spectrometry and other analytical methods, can meet the needs of trace detection, but these methods are expensive in equipment, time-consuming and energy-consuming in detection, and high in cost, and do not meet the needs of on-site rapid detection. An immuno-detection method is fast, sensitive and suitable for on-site detection, and provides a new choice for the detection of mercury and other heavy metals. The present invention uses gold-nanoflower particles to label antibodies to prepare probes for immunodetection, and combines an immunochromatographic strip technology to develop a nanoflower immunochromatographic strip. The immunochromatographic strip has simple assembly, strong specificity, only competition for $Hg^{2+}$, no cross-reaction with other metal ions, good stability, high sensitivity, excellent repeatability and a detection limit lower than national food safety standards, and can effectively and accurately detect residual heavy metal mercury ions in grains, which has important practical significance for safety monitoring of heavy metal residues in grains.

SUMMARY

The present invention provides a nanoflower immunochromatographic strip for detecting heavy metal mercury ions and a use thereof aiming at solving the above problems. The nanoflower immunochromatographic strip of the present invention has strong specificity, high sensitivity and good stability, and can be used for rapid detection of mercury ions in cereals.

In order to achieve the above purpose, the present invention adopts the following technical solution.

A nanoflower immunochromatographic strip for detecting heavy metal mercury ions, wherein the nanoflower immunochromatographic strip includes the following components: a plastic outer shell, a sample pad, an immunoprobe joint pad, a nitrocellulose (NC) membrane, and an absorbent pad; the immunoprobe joint pad is dropwise added with gold nano-immunoprobe labeled with anti-mercury-ion monoclonal antibody; the anti-mercury-ion monoclonal antibody is a monoclonal antibody secreted by a murine hybridoma cell strain 7A1 and the murine hybridoma cell strain 7A1 has been preserved in the China General Microbiological Culture Collection Center, with a preservation address at No. 3, Yard 1, Beichen West Road, Chaoyang District, Beijing, a preservation date on Nov. 23, 2021 and a preservation number of CGMCC No. 23879.

A preparation method of the above nanoflower immunochromatographic strip for detecting heavy metal mercury ions includes the following steps:

(1) preparation of a gold-nanoflower solution: adding 100 mL of double-distilled water into a 250 mL high-temperature sterilized conical flask soaked in aqua regia and washed, adjusting pH to 7.5 with 1M NaOH; under a stirring condition, sequentially adding 750 μL of a 1 wt % chloroauric acid, 500 μL of a colloidal gold as a seed, 300 μL of a 1 wt % trisodium citrate, and 1 mL of a newly prepared 0.03 M hydroquinone solution, and continuing to stir until a stable blue solution is obtained, so as to obtain the gold-nanoflower solution;

(2) preparation of an immunoprobe: taking and putting 10 mL of the gold-nanoflower solution into a high-temperature sterilized narrow-mouthed bottle, under an ice bath, adding and evenly stirring 60 μL of 0.1 M $K_2CO_3$, then dropwise adding 60 μL of a 1.25 mg/mL anti-mercury-ion monoclonal antibody, continuing to stir for 1 hour, then adding a BSA according to 1% of a total volume, continuing to stir for 30 minutes under the ice bath, then adding PEG 20000 according to 0.5% of the total volume, continuing to stir for 30 minutes under the ice bath, and finally sealing and putting a labeled solution in a 4° C. refrigerator for equilibrium overnight to obtain a gold nano-immunoprobe labeled with the anti-mercury-ion monoclonal antibody (AuNF-mAb), wherein a preparation method of the anti-mercury-ion monoclonal antibody is as follows: injecting a murine hybridoma cell strain 7A1 in a logarithmic growth period into abdominal cavities of paraffin-sensitized 9-week-old female Balb/c mice by $1×10^6$ cells/mouse, and collecting ascites when abdomens of the mice are swollen and tense, and separating and purifying the ascites to obtain an anti-$Hg^{2+}$-ITCBE monoclonal antibody;

(3) pretreatment of the immunoprobe joint pad and the sample pad: cutting an untreated immunoprobe joint pad and an untreated sample pad into 1.3 cm-width long strips with scissors, putting the 1.3 cm-width long strips in a large culture dish, submerging the 1.3 cm-width long strips with a blocking solution prepared in advance, then transferring the 1.3 cm-width long strips to a 37° C. thermostatic incubator for blocking for 2 hours, removing the 1.3 cm-width long strips from the 37° C. thermostatic incubator, filtering the blocking solution and continuing to put the 1.3 cm-width long strips in the 37° C. thermostatic incubator for drying, and storing the 1.3 cm-width long strips at 4° C. after drying, wherein for subsequent use, cutting is carried out according to a length of 1.3 cm and a width of 4 mm, and the blocking solution comprises 5 wt % BSA and 1 vol % Tween-20;

(4) NC membrane streaking: taking and streaking a goat anti-mouse secondary antibody on the NC membrane, a final concentration of the goat anti-mouse secondary antibody streaked on a line C being 0.53 ng/cm, and after cutting, a content of the goat anti-mouse secondary antibody streaked on each 4 mm-width card strip being 0.212 ng; taking and streaking a complete antigen $Hg^{2+}$-ITCBE-BSA on the NC membrane, a final concentration of the complete antigen $Hg^{2+}$-ITCBE-BSA streaked on a line T being 0.043 ng/cm, and after cutting, a content of the complete antigen $Hg^{2+}$-ITCBE-BSA on each 4 mm-width card strip being 0.0172 ng, namely the line T, wherein on the NC membrane, a distance between the line C and the line T is 0.5 cm;

(5) preparation of the immunoprobe joint pad: dropwise adding 3 μL of the gold nano-immunoprobe labeled with the anti-mercury-ion monoclonal antibody prepared in step (2) on a pretreated immunoprobe joint pad;

(6) assembly of the nanoflower immunochromatographic strip: sequentially assembling the NC membrane streaked in step (4), the immunoprobe joint pad prepared in step (5), the sample pad and the absorbent pad pretreated in step (3) on a bottom pad, wherein the immunoprobe joint pad and the sample pad are sticked in overlapped and staggered modes, the same ends of the immunoprobe joint pad and the sample pad are spaced by 2 mm, and the absorbent pad and the NC membrane are overlapped by 2 mm in a head-to-tail mode; covering the plastic outer shell with a cover, and drying, encapsulating and storing the nanoflower immunochromatographic strip at 4° C.

A use of the above nanoflower immunochromatographic strip for detecting heavy metal mercury ions in detection of heavy metal mercury ions.

A detection principle of a nanoflower immunochromatographic strip for detecting heavy metal mercury ions is as follows: when a strip is used for detection, firstly a prepared gold-labeled probe is dropwise added onto a gold-labeled pad, after drying, assembly is then carried out according to an assembly way shown in a schematic diagram (FIG. 1), a sample is dropwise added onto a sample pad, a liquid flows to one end of an absorbent paper through an action of chromatography, when passing through a line T, the gold-labeled probe that is not combined with an antigen in the sample will be combined with a complete antigen on the line T and will stay at the line T, resulting in that color rendering will occur on the line T, the liquid continues to flow forward, when passing through a line C, the gold-labeled probe that is combined or not combined with the antigen in the sample will be combined with the line C until saturated, and the combined gold-labeled probe will stay at the line C, resulting in that color rendering will occur on the line C. A whole color reaction takes about 10 minutes.

The present invention has the following beneficial effects.

(1) The present invention develops a nanoflower immunochromatographic strip for detecting heavy metal mercury ions. The nanoflower immunochromatographic strip can detect the content of heavy metal mercury ions in cereals, a detection threshold is 50 ng/mL, and a minimum detection limit is 1.56 ng/mL under visible conditions; under the detection condition of a card reader, a minimum detection limit is 0.39 ng/mL, and a detection time is only 5 minutes.

(2) The present invention provides a cell strain for a monoclonal antibody against heavy metal mercury ions, an affinity constant Kaff is determined to be $7.2\times10^9$ L/mol, the cell strain has high affinity and can better recognize a mercury ion hapten, and a 50% mercury ion inhibition rate IC50 is 37.426 ng/mL.

BRIEF DESCRIPTION OF THE DRAWINGS

FIG. 3A: Mouse tail blood titer; FIG. 3B: Mouse tail blood competition.

FIG. 10A: Full-wavelength scanning diagram; FIG. 10B: TEM diagram.

FIGS. 11A-11B show determination of an optimal antibody amount and an optimal pH for gold-nanoflower labeling. FIG. 11A: An optimal amount of an antibody for gold-nanoflower labeling is 4.98 μg/mL; FIG. 11B: An optimal pH for labeling a gold-nanoflower system with the antibody is 6.5.

FIGS. 12A-12B show selection of a best line C and a best line T of a gold-nanoflower labeled antibody. FIG. 12A: A concentration of the best line C is 0.53 μg/cm; FIG. 12B: A concentration of the best line T is 0.043 μg/cm.

FIG. 13A: Determination of specificity of nanoflower immunochromatographic strips; FIG. 13B: Determination of line T values by an immune card reader.

FIG. 14A: Determination of sensitivity of immunochromatographic strips; FIG. 14B: Determination of sensitivity values by an immune card reader.

DETAILED DESCRIPTION OF THE EMBODIMENTS

The present invention is further described below in connection with specific embodiments. The schematic embodiments and the descriptions of invention herein are used to explain the present invention, but are not to be considered as limitations of the present invention.

Figure 1:
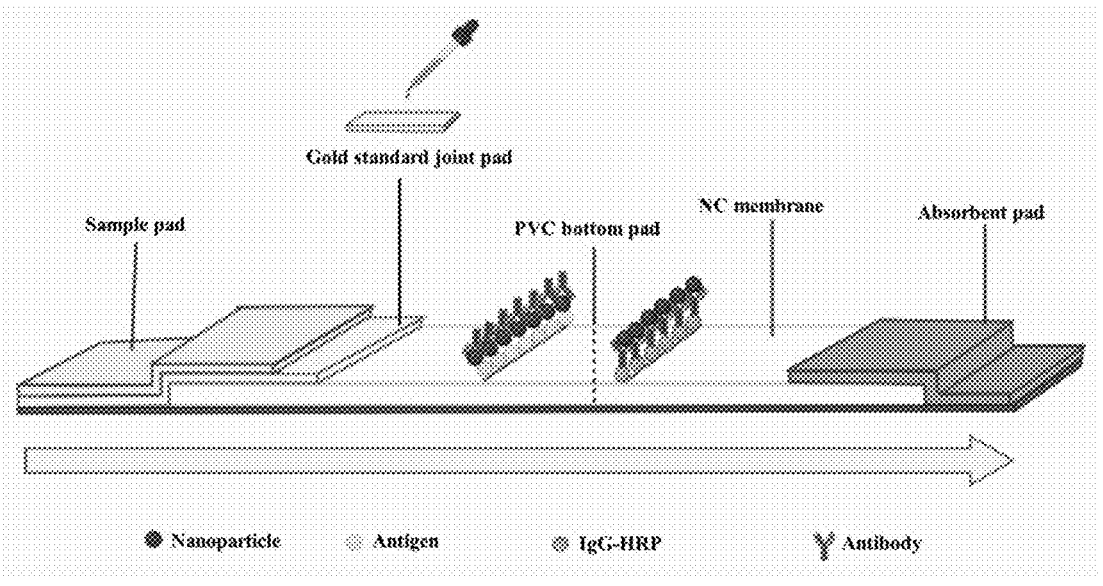
FIG. 1 shows a structural model of a nanoflower immunochromatographic strip.
Figure 2:
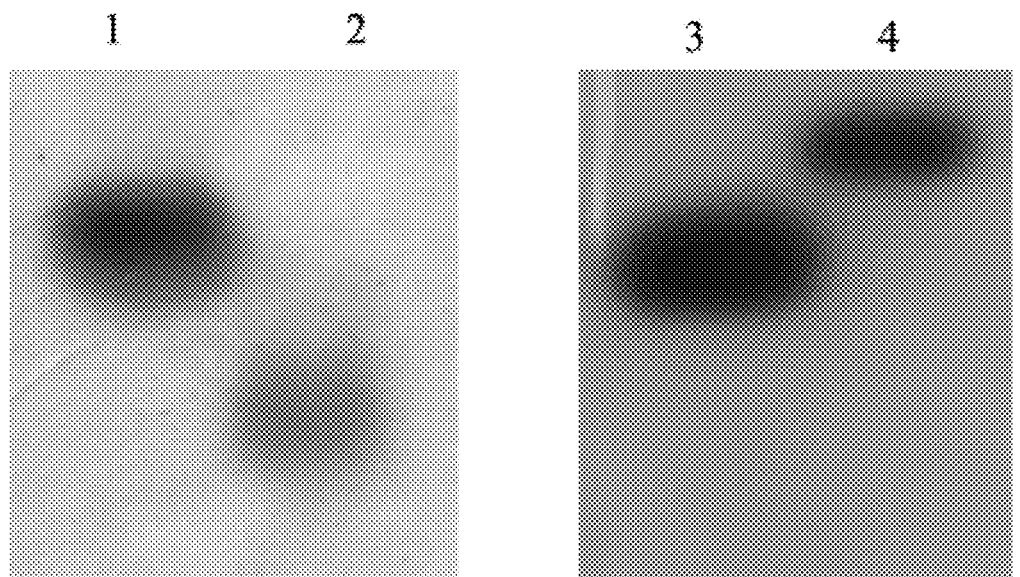
FIG. 2 shows an agarose gel electrophoresis analysis of an antigen conjugate. Lane 1: KLH. Lane 2: $Hg^{2+}$-ITCBE-KLH. Lane 3: $Hg^{2+}$-ITCBE-BSA. Lane 4: BSA.

Example 1 Screening of Anti-Mercury-Ion Monoclonal Cell Strain 7A1 and Preparation of Antibody 1. Preparation of Artificial Complete Antigen 10 mg of hemocyanin KLH was taken and dissolved in 1 mL of an HBS buffer solution and adjusted to pH=8 with 1 mol/mL NaOH, then 10 mg of 1-(4-isothiocyanatobenzyl) ethylenediamine-N,N,N,N-tetraacetic acid (ITCBE) was then added, after well mixing, cross-linking was conducted overnight in dark at 180 r/min at a room temperature to obtain a hapten, 130 μL of a mercury ion standard solution (1 mg/mL) was then dropwise added slowly, cross-linking was conducted in the dark at 180 r/min for reaction for 6 hours, dialysis was conducted for two days with 0.01 M PBS (18.0 g of NaCl; 0.2 g of KCl; 1.44 g of $Na_2HPO_4$; 0.24 g of $KH_2PO_4$; distilled water was added to 1000 ml, pH was adjusted to 7.4), a dialyzate was changed every 4 hours, and after dialysis, concentration was conducted with PEG 20000 to obtain an immune antigen $Hg^{2+}$-ITCBE-KLH. The hemocyanin KLH was replaced with a bovine serum albumin (BSA) to prepare a detection antigen $Hg^{2+}$-ITCBE-BSA, by following the same preparation process mentioned above (FIG. 2).

2. Animal Immunization

Figure 3A:
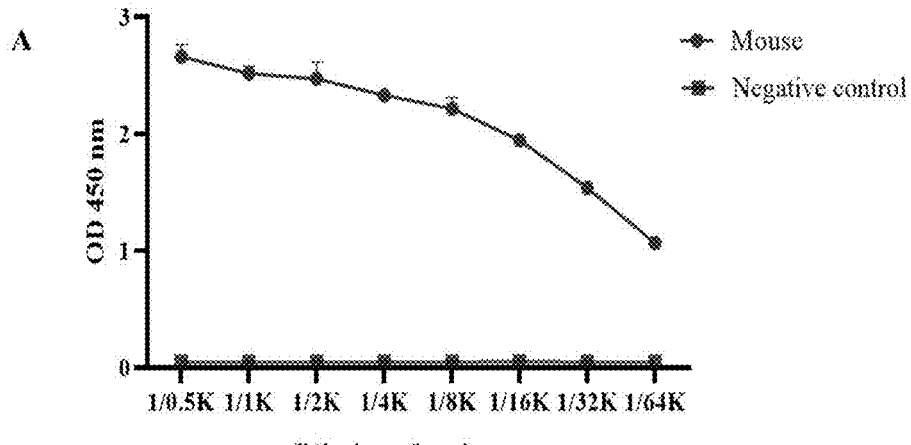
FIGS. 3A-3B show determination of mouse tail blood titer and icELISA.
Figure 3B:
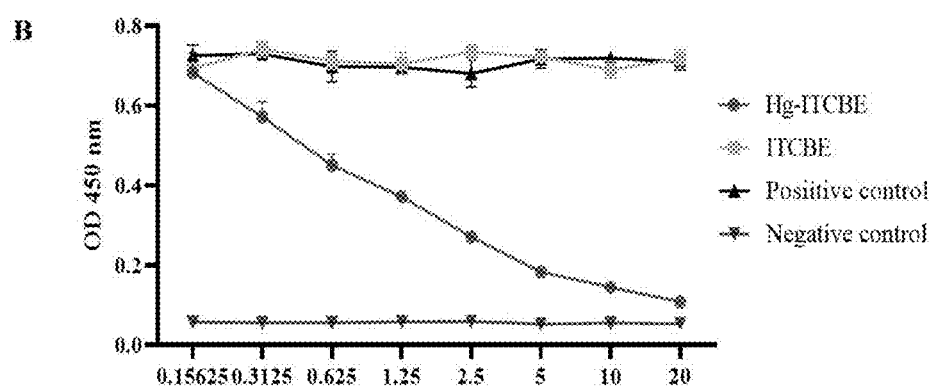

Six-week-old Balb/c mice were immunized with the artificial complete antigen $Hg^{2+}$-ITCBE-KLH an immune antigen. The $Hg^{2+}$-ITCBE-KLH was taken and mixed well with an equal volume of Freund's complete adjuvant, and each mouse was subjected to subcutaneous multi-point injection at the neck and back of the mouse in an amount of 100 μg/200 μL after suction by a vortex oscillator and a syringe in combination with complete emulsification. For subsequent immunization, the immune antigen was taken and mixed with a Freund's incomplete adjuvant at 1:1 for complete emulsification, and each mouse was injected subcutaneously with 50 μg/200 μL at different sites, and each immunization interval was 14 days. Beginning with the fourth immunization, within 5 to 7 days after each immunization, blood was collected from tail veins, and serums were separated. The titer of the mouse serums was detected by indirect enzyme-linked immunosorbent assay (ELISA), and the IC50 of the mouse serums was determined by indirect competitive ELISA (FIGS. 3A-3B). Mice with relatively good titer and IC50 were selected, and subjected to intraperitoneal injection with the immune antigen $Hg^{2+}$-ITCBE-KLH twice the previous immune dose diluted to 500 μL with normal saline, to conduct the final booster immunization. The above indirect ELISA and indirect competitive ELISA are conventional ELISA operations.

3. Cell Fusion

3 To 4 days after the last booster immunization, spleen cells were collected from the mice, 50% polyethylene glycol 1450 (PEG 1450) was used as a fusion agent, the spleen cells and SP2/0 myeloma cells were mixed in 20 mL of a fresh RPMI 1640 incomplete culture medium according to the number of cells in 4:1, gently mixed well and then centrifuged at 1,100 rpm for 7 minutes, a supernatant was discarded, a centrifuge tube was gently flicked to loosen the cells at a bottom, and then placed in a 37° C. water bath, 1 mL of 50% PEG 1450 preheated at 37° C. was dropwise added slowly first and then quickly within 1 minute, the centrifuge tube was shaken while adding to promote cell contact, the centrifuge tube was made to stand for 0.5 minute, 1 mL of an RPMI 1640 incomplete culture solution was then added slowly in the first minute, and the RPMI 1640 incomplete culture solution was replenished slowly first and then quickly to 40 mL within 2 minutes, to terminate an effect of PEG; centrifugation was conducted at 1,000 rpm for 10 minutes, a supernatant was discarded, 5 mL of a fresh culture medium was added and gently mixed well, and a cell suspension was transferred onto 95 mL of a complete culture medium containing 2% HAT (an RPMI 1640 culture medium containing 20% FBS), mixed well, and then plated on a 96-well plate with pre-plated feeder layer cells (including approximately 2,000 feeder layer cells per well and an RPMI 1640 culture medium containing 10% FBS), with 100 μL per well; and the complete culture medium containing 2% HAT was replaced after 15 days of fusion. After the cells grew to the 5th to 7th day after fusion, 100 μL of a supernatant was sucked from each well, 120 μL of the complete culture medium containing 2% HAT (the RPMI 1640 culture medium containing 20% FBS) was replenished, on the 10th to 12th day after fusion, screening was conducted in two steps by ELISA, the first step referred to screening positive wells of anti-$Hg^{2+}$-ITCBE without anti-carrier protein by indirect ELISA; the second step referred to conducting indirect competitive ELISA on the positive wells screened in the first step by using $Hg^{2+}$-ITCBE as a competitive antigen by indirect competitive ELISA; wells with high absorbance value and high sensitivity were selected (the absorbance value here referred to a first-step detection result of the same cell well; the sensitivity here referred to a concentration of the competitive antigen when an inhibition rate was 50%, namely a second-step detection result of the same cell well), and subcloning was conducted by limiting dilution assay. 7 To 8 days after the first subcloning, detection was conducted by adopting the same two-step screening, and wells with high absorbance value and high sensitivity were selected. The rest wells were detected only by indirect ELISA 10 to 12 days after subcloning, and wells with high absorbance value were selected. Subcloning was repeated 2 to 3 times until a positive rate of 100% was achieved to obtain a murine hybridoma cell strain 7A1.

The murine hybridoma cell strain 7A1 has been preserved in the China General Microbiological Culture Collection Center, with a preservation address at No. 3, Yard 1, Beichen West Road, Chaoyang District, Beijing, a preservation date on Nov. 23, 2021 and a preservation number of CGMCC No. 23879.

4. Antibody Subtype Identification

Figure 4:
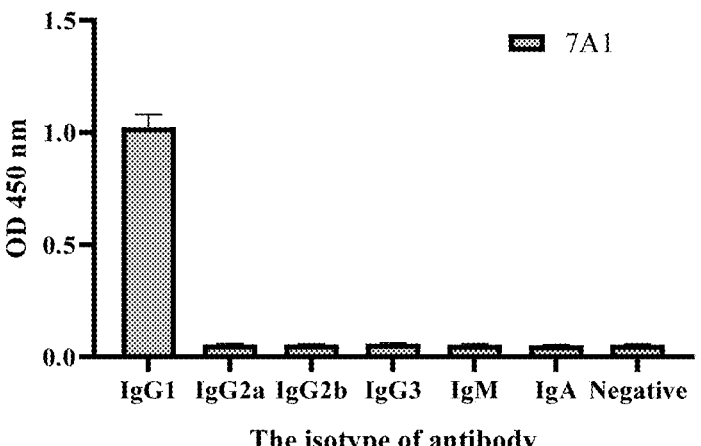
FIG. 4 shows identification of a subtype of a 7A1 monoclonal antibody.

An anti-$Hg^{2+}$-ITCBE monoclonal antibody secreted by the hybridoma cell strain 7A1 was identified with a commercially available subtype determination kit (Manufacturer: SIGMA, Article Number: ISO2-1KT). Identification results were shown in FIG. 4, and the cell strain was a subtype IgG1.

Example 2 Preparation and Property Identification of Anti-$Hg^{2+}$-ITCBE Monoclonal Antibody 1. Preparation and Purification of Ascites 1) Preparation of Ascites A murine hybridoma cell strain 7A1 in a logarithmic growth period was injected into abdominal cavities of paraffin (500 μL/mouse)-sensitized 9-week-old female Balb/c mice at approximately $1 \times 10^6$ cells/mouse. After one week, the mice were observed, ascites was collected when abdomens of the mice were swollen and tense, and centrifuged at 4° C. at 13,000 r/min for 20 minutes, after centrifugation, the ascites was divided into three layers (from bottom to top, sequentially including an aggregate, a middle layer containing a lot of antibodies, and a lipid layer), and the middle layer was collected.

2) Antibody Purification

Figure 5:
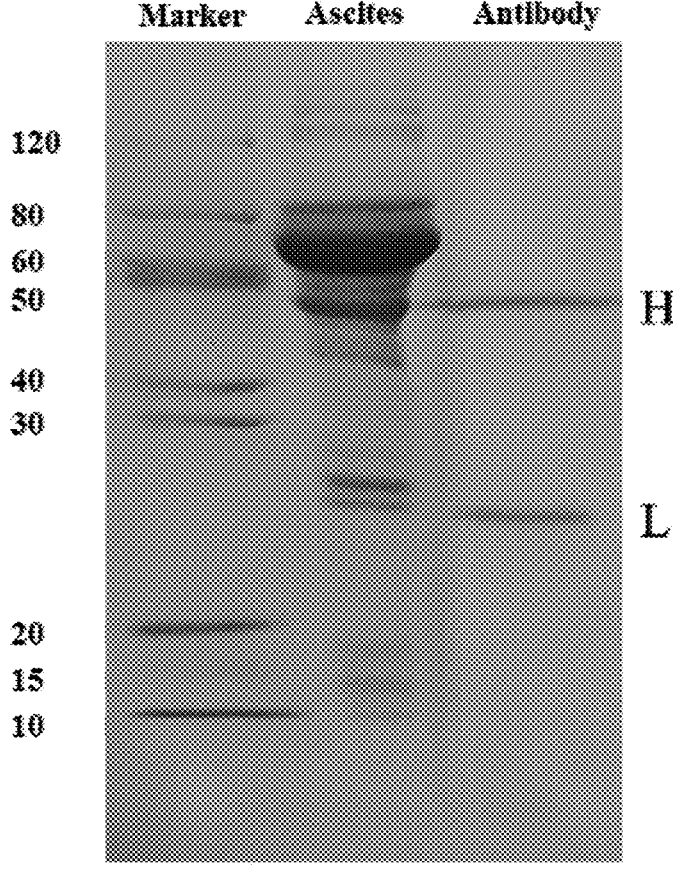
FIG. 5 shows identification of purification results of a 7A1 monoclonal antibody by SDS-PAGE.

The ascites was diluted with a balance buffer solution (3.5814 g/L of $Na_2HPO_4$, 4.383 g/L of NaCl, pH 7.0) at 1:10. The diluted ascites was filtered with 0.45 μm and then subjected to Protein G affinity chromatography column, and operation was conducted according to commercial Protein G affinity chromatography instructions. A purified antibody was sequentially dialyzed for 3 days in a dialysis bag with PBS (8.0 g of NaCl; 0.2 g of KCl; 1.44 g of $Na_2HPO_4$; 0.24 g of $KH_2PO_4$; adding distilled water to 1,000 ml, adjusting pH to 7.4), dialyzed for 1 day with ultrapure water, and finally concentrated with PEG 20000, to obtain an anti-$Hg^{2+}$-ITCBE monoclonal antibody, which was stored in a −20° C. refrigerator for standby. The purity of the antibody was detected and verified by 13% SDS-PAGE, as shown in FIG. 5, the purified antibody had bands at both 25 kDa and 50 kDa, which respectively corresponded to a light chain and a heavy chain of an IgG antibody, and there were almost no heterobands, indicating that a purification effect was good. After complete dialysis with ultrapure water, freezing and drying were conducted, and freeze-dried powder was collected to obtain an anti-divalent-mercury-ion monoclonal antibody 7A1, which was put in a −20° C. refrigerator for standby.

Figure 6:
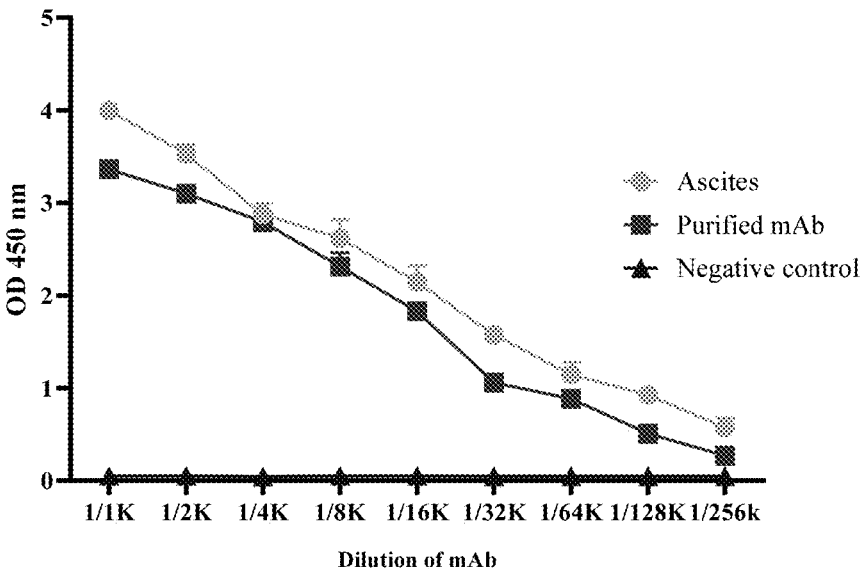
FIG. 6 shows a titer map of a purified antibody and ascites.

3) Titer determination: the titer of the ascites and the titer of the purified antibody were determined by conventional non-competitive ELISA, results were shown in FIG. 6, the titer of the ascites exceeded $1.28×10^5$, and the titer of the purified antibody exceeded $0.64×10^5$, indicating that the purified antibody still maintained high activity.

2. Characterization Identification of Monoclonal Antibody

1) Affinity Determination

Figure 7:
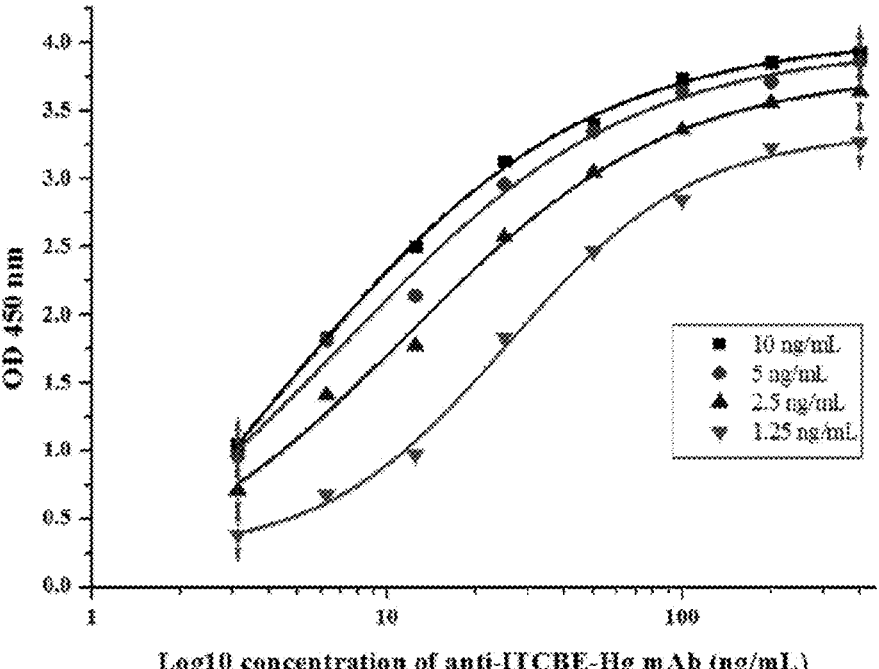
FIG. 7 shows determination of affinity of a monoclonal antibody.

According to Beatty's method, an affinity constant Kaff of a monoclonal antibody was determined by indirect ELISA. $Hg^{2+}$-ITCBE-BSA was diluted to 10 μg/mL, 5 μg/mL, 2.5 μg/mL and 1.25 μg/mL for coating on ELISA plates with ELISA coating buffer solutions, and the rest steps were performed by conventional indirect ELISA. Analysis was conducted by Origin 8.0, as shown in FIG. 7, the affinity constant of the antibody was calculated according to the following formula, and a calculation result was $7.3×10^9$ L/mol, indicating a high-affinity antibody.

$$Kaff = \frac{n-1}{2 \times (n[Ab]t - [Ab])}$$

where [Ab] represents an antibody concentration at IC50 when an antigen concentration is [Ag];

[Ab]t represents an antibody concentration at IC50 when an antigen concentration is [Ag]t;

$n=[Ag]/[Ag]t$

2) Analysis of Cross Reactivity of Antibody

Figure 8:
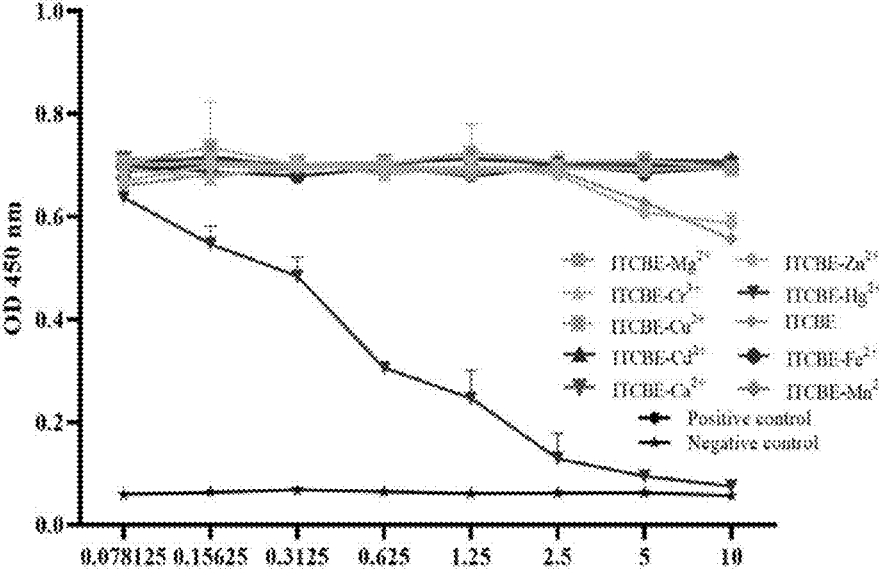
FIG. 8 shows analysis of cross-reactivity of an antibody.

A detection antigen $Hg^{2+}$-ITCBE-BS with 5 μg/mL was used for coating on ELISA plates, ITCBEs chelated with standards of nine metal ions $Hg^{2+}$, $Zn^{2+}$, $Mg^{2+}$, $Cu^{2+}$, $Ca^{2+}$, $Mn^{2+}$, $Fe^{2+}$, $Cd^{2+}$ and $Cr^{3+}$ as well as ITCBE were used as competitive antigens respectively, the 10 competitive antigens were diluted at 200 ng/mL respectively, the antibody 7A1 was diluted at 1:64k, specificity was determined by conventional indirect competitive ELISA, and results were shown in FIG. 8.

3) Antibody Sensitivity Determination

Figure 9A:
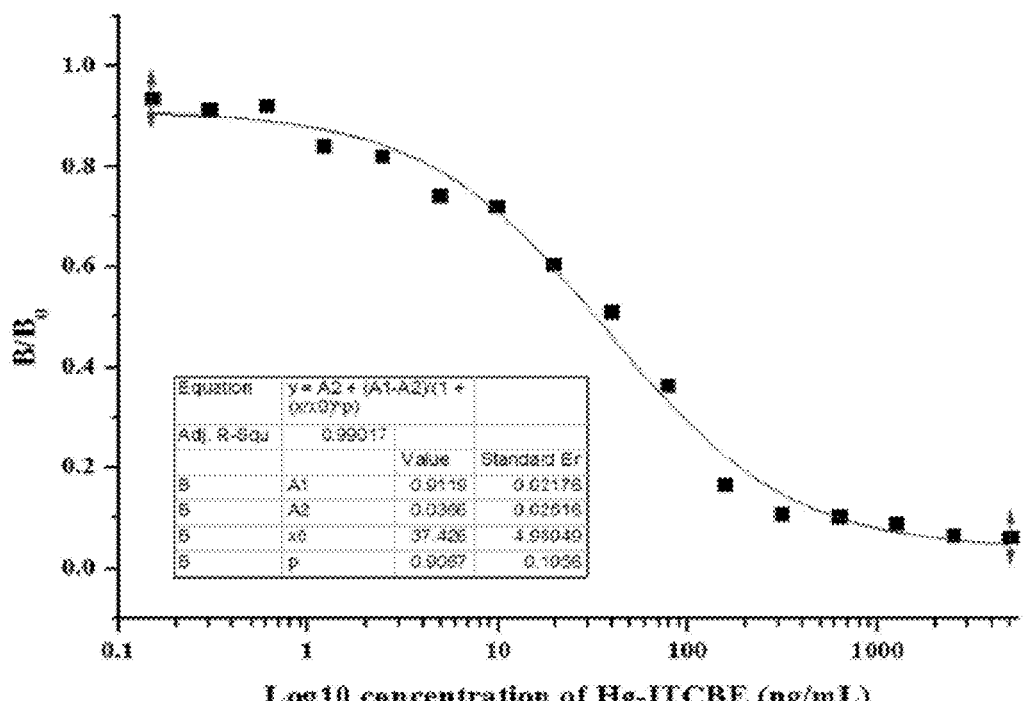
FIGS. 9A-9B show drawings of competitive curves of an anti-$Hg^{2+}$-ITCBE monoclonal antibody.
Figure 9B:
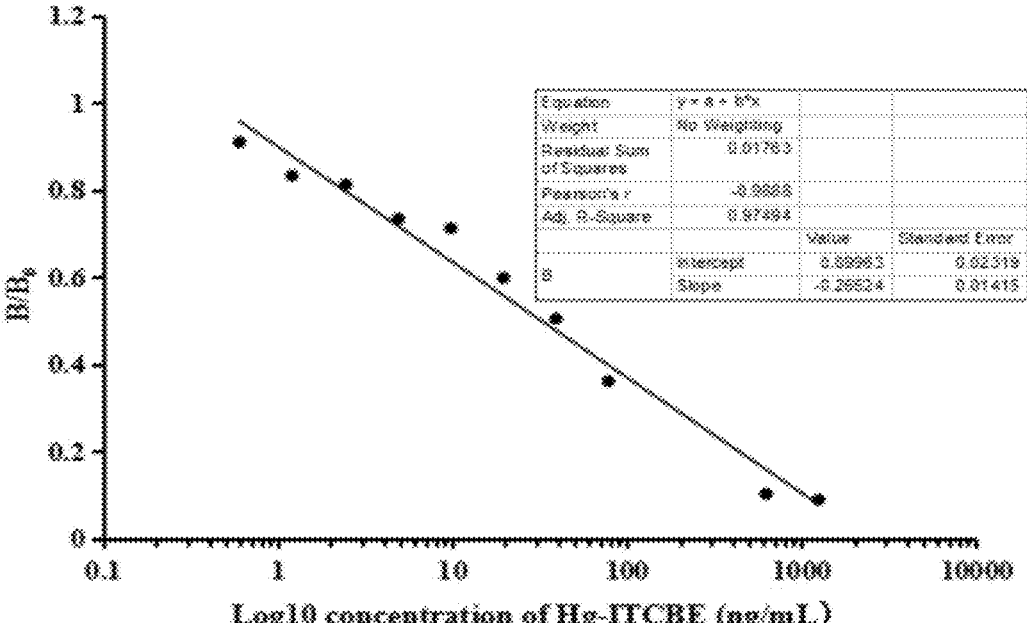

The sensitivity to $Hg^{2+}$-ITCBE was determined by conventional indirect competitive ELISA, a standard competitive curve was drawn, results were shown in FIG. 9A, a curve equation $y=0.0366+\{0.8753/[1+(x/37.426)^{0.9067}]\}$, $R^2=0.99017$, where IC50=37.426 ng/mL, a good linear relationship was shown between IC10 and IC90, a linear equation of a linear part was $y=0.89963-0.26524x$, $R^2=0.97494$, results were shown in FIG. 9B, and a linear range was 0.00099 to 1.024 μg/mL.

Figure 10A:
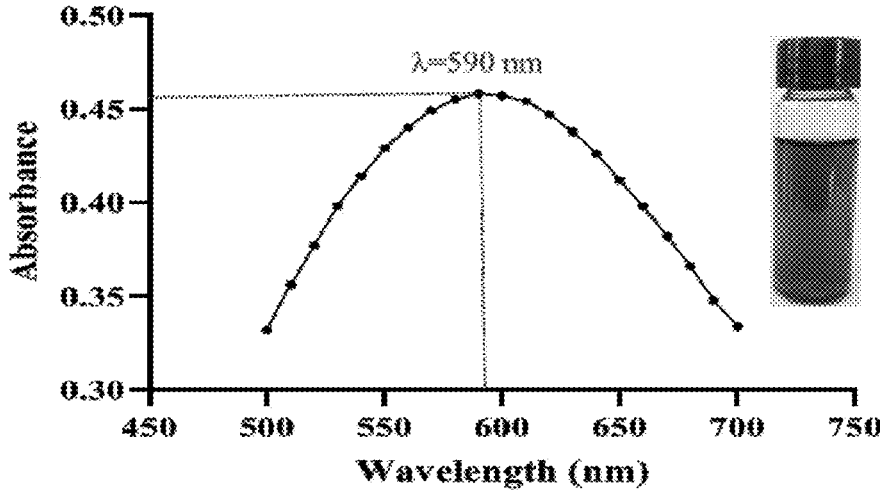
FIGS. 10A-10B show an ultraviolet full-wavelength scanning diagram and a TEM diagram of a gold-nanoflower solution.
Figure 10B:

Example 3 Development of Nanoflower Immunochromatographic Strip (1) Preparation of Gold-Nanoflower Working Solution A 250 mL high-temperature sterilized conical flask soaked in acid anhydride and washed was prepared, 100 mL of double distilled water was added, and pH was adjusted to approximately 7.5 with 1M NaOH. Under a stirring condition, 750 μL of a 1 wt % chloroauric acid, 500 μL of a colloidal gold as a seed, 300 μL of a 1 wt % trisodium citrate and 1 mL of a newly prepared 0.03 M hydroquinone solution were sequentially added, and stirred until a stable blue solution was obtained to obtain a gold-nanoflower solution. Next, the prepared gold-nanoflower solution was scanned by a microplate reader with a scanning range of 400 to 900 nm, and its maximum absorption peak wavelength was observed (see FIG. 10A). The prepared gold-nanoflower solution was further subjected to scanning electron microscope (SEM) to observe the size of gold-nanoflower particles and calculate an average diameter (see FIG. 10B). Then, the prepared solution was sealed and stored in a 4° C. refrigerator.

(2) Labeling of Gold-Nanoflower Immunoprobe

1) Determination of Optimal Antibody Amount for Gold-Nanoflower Labeling

Firstly, 200 μL of the gold-nanoflower working solution was added into each of 8 ELISA wells, the first well was used as a blank control, 1 μL of a 1.25 mg/mL anti-mercury-ion ($Hg^{2+}$-ITCBE) monoclonal antibody was added into the second well, and then 2 μL, 3 μL, 4 μL, 5 μL, 6 μL and 7 μL of the anti-mercury-ion monoclonal antibody were added into the remaining 6 wells in sequence, mixing was conducted well by a pipette, and they were placed in a 37° C. thermostatic incubator to stand for 30 minutes. Then, 20 μL of a 10 wt % NaCl solution was added into each well, after well mixing, standing continued for 5 minutes in the 37° C. thermostatic incubator, after taking out, the color change of the gold-nanoflower working solution was observed, and the absorbance at 590 nm of each well was detected by a microplate reader (see FIG. 11A). Results showed that: when 1 μL of the anti-mercury-ion monoclonal antibody was added, the absorbance could reach a maximum value at $OD_{590}$ nm, and the solution color of this well basically had no obvious change compared with the control group, indicating that the gold-nanoflower working solution system was the most stable when 1 μL of the anti-mercury-ion monoclonal antibody was added.

2) Determination of Optimal pH for Gold-Nanoflower Labeling

After the amount of a labeled antibody was optimized, the pH of the working solution when antibody labeling was further optimized, including the following steps: firstly, 200 μL of the gold-nanoflower working solution was added into each of 8 ELISA wells respectively, and 1 μL (1.25 mg/mL) of the previously determined optimal antibody amount was added into the above gold-nanoflower working solution, and gently mixed well by a pipette. The first well was used as blank control, 1 μL of a 0.1 M $K_2CO_3$ solution was added into the second well, and then 2 μL, 3 μL, 4 μL, 5 μL, 6 μL and 7 μL of the 0.1 M $K_2CO_3$ solution were added into the remaining 6 wells in sequence, and after well mixing, they were placed in a 37° C. thermostatic incubator to stand for 30 minutes. Then, 20 μL of a 10% NaCl solution was added into each well, after well mixing, standing continued for 5 minutes at 37° C., the color change of the gold-nanoflower working solution was observed, and the absorbance at $OD_{590}$ nm of each well was detected by a microplate reader (see FIG. 11B). Results showed that: when 1 μL of the 0.1 M $K_2CO_3$ solution was added, the absorbance could reach a maximum value at $OD_{590}$ nm, and the solution color of this well basically had no obvious change compared with the control group, indicating that the nanoflower working solution system was the most stable when 1 μL of the 0.1 M $K_2CO_3$ solution was added.

(3) Labeling Anti-Mercury-Ion Monoclonal Antibody with Gold-Nanoflower 10 mL of the gold-nanoflower working solution was taken and put into a 20 mL high-temperature sterilized narrow-mouthed bottle, under an ice bath, 60 μL of the $K_2CO_3$ with the optimal amount (0.1 M) was added (considering the loss of antibody in the process of sample adding or labeling, the optimal amount of the antibody was added according to 1.2 times the volume dose), and evenly stirred, 60 μL of the antibody with the optimal labeling amount was then added dropwise, and continued to be stirred for 1 hour, 0.1012 g of a BSA was then added according to 1% of a total volume, under the ice bath, stirring continued for 30 minutes, 0.0506 g of PEG20000 was then added according to 0.5% of the total volume, under the ice bath, stirring continued for 30 minutes, and finally, a labeled solution was sealed and put in a 4° C. refrigerator for equilibrium overnight.

(4) Selection of Optimal Conditions of Gold-Nanoflower Rapid Detection Test Strip 1) Treatment of Probe Joint Pad and Sample Pad An untreated gold-labeled pad and an untreated sample pad were cut into 1.3 cm-width long strips with scissors, and the long strips were put in a large culture dish, submerged with a blocking solution (5% BSA and 1% Tween-20) prepared in advance, and then transferred to a 37° C. thermostatic incubator for blocking for 2 hours. After the long strips were removed from the thermostatic incubator, the blocking solution was filtered, and the long strips continued to be put in the thermostatic incubator for drying, and stored at 4° C. after drying. For subsequent use, cutting was carried out according to a length of 1.3 cm and a width of 4 mm.

2) Selection of Best Dilution of Line C of Test Strip 2 mg/mL of a goat anti-mouse secondary antibody was diluted with 0.01 M PBS according to a final concentration of a line C, and finally diluted to four concentrations of 1.33 μg/mL, 0.89 μg/mL, 0.67 μg/mL and 0.53 μg/mL, and 10 μL of the goat anti-mouse secondary antibody of each concentration was taken and streaked on a NC membrane. When streaking was conducted by an ion sputter coater, streaking was repeated 5 times at a streaking speed of 0.2 μL/cm, and the final concentrations streaked on the line C were 1.33 ng/cm, 0.89 ng/cm, 0.67 ng/cm and 0.53 ng/cm respectively. The NC membrane after streaking was put in a 37° C. thermostatic incubator for drying for 15 minutes, and then cut into strips with a width of 4 mm. After cutting, contents of the goat anti-mouse secondary antibody on each 4 mm-width strip was 0.532 ng, 0.356 ng, 0.268 ng and 0.212 ng respectively. Next, 3 μL of a gold-labeled probe was dropwise added onto each of four assembled immunochromatographic strips, and 100 μL of 0.01 M PBS was dropwise added slowly on the sample pad. The strips were placed at a room temperature for reaction for 10 minutes. The degree of color of the line C of the strips was observed, and finally through observation, a concentration of 0.53 ng/cm (that is, the content of the goat anti-mouse secondary antibody on each strip with a width of 4 mm after cutting was 0.212 ng) was selected as the best line-C streaking concentration (FIG. 12A).

3) Selection of Best Dilution of Line T of Test Strip

A complete antigen $Hg^{2+}$-ITCBE-BSA was diluted with 0.01 M PBS according to a final concentration of a line T, and finally diluted to five concentrations of 0.21 μg/mL, 0.11 μg/mL, 0.071 μg/mL, 0.053 μg/mL and 0.043 μg/mL, and 10 μL of the complete antigen $Hg^{2+}$-ITCBE-BSA of each concentration was taken and streaked on a NC membrane. When streaking was conducted by an ion sputter coater, streaking was repeated 5 times according to a streaking speed of 0.2 μL/cm, and the final concentrations streaked on the line T were 0.21 ng/cm, 0.11 ng/cm, 0.071 ng/cm, 0.053 ng/cm and 0.043 ng/cm respectively. The NC membrane after streaking was put in a 37° C. thermostatic incubator for drying for 15 minutes, and then cut into strips with a width of 4 mm. After cutting, contents of the antigen on each 4 mm-width strip were 0.084 ng, 0.044 ng, 0.0284 ng, 0.0212 ng and 0.0172 ng respectively. Next, 3 μL of a gold-labeled probe was dropwise added onto each of five assembled immunochromatographic strips, and 100 μL of 0.01 M PBS was dropwise added slowly on the sample pad. The strips were placed at room temperature for reaction for 10 minutes. The degree of color of the line T of the strips was observed, and finally through observation, a concentration of 0.043 ng/cm (that is, the content of the complete antigen $Hg^{2+}$-ITCBE-BSA on each strip with a width of 4 mm after cutting was 0.0172 ng) was selected as the best line-T streaking concentration (FIG. 12B).

(5) Test of Gold-Nanoflower Rapid Detection Test Strip

1) Determination of Specificity of Gold-Nanoflower Chromatographic Strip

Figure 13A:
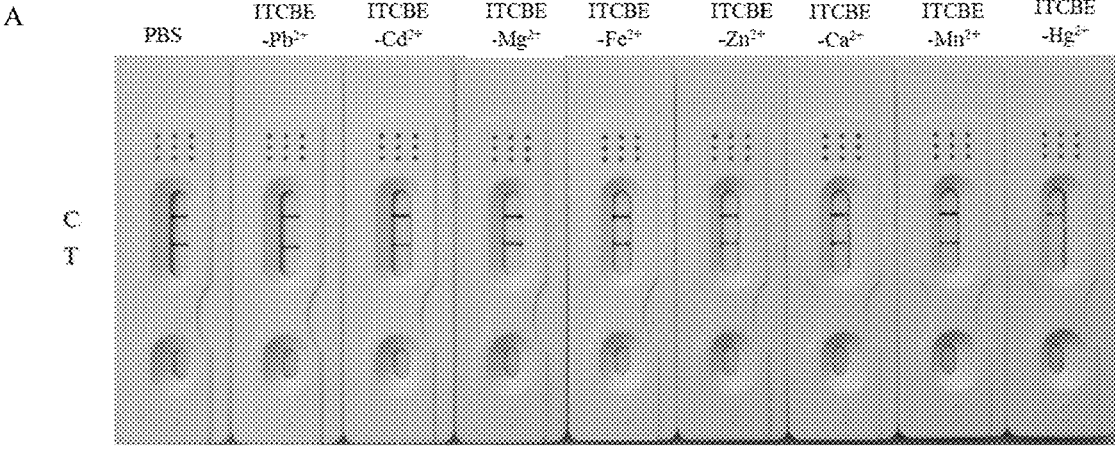
FIGS. 13A-13B show determination of specificity of the nanoflower immunochromatographic strip.
Figure 13B:
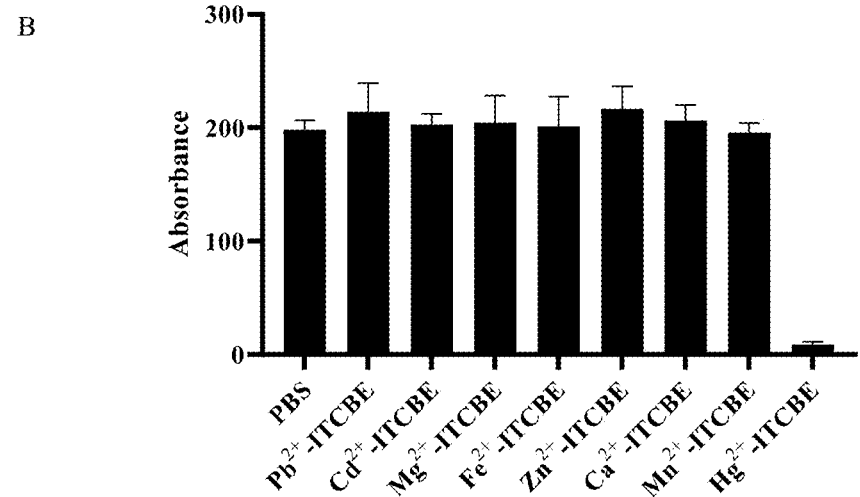

Streaking was conducted simultaneously on the NC membrane according to the above optimized dilution ratio of the best line C and the best line T, and the NC membrane after streaking was put in a 37° C. thermostatic incubator for drying for 15 minutes and then cut into strips. Next, 3 μL of an immunoprobe was dropwise added on a probe joint pad, and a test strip was assembled well. $Hg^{2+}$-ITCBE, $Ca^{2+}$-ITCBE, $Mg^{2+}$-ITCBE, $Mn^{2+}$-ITCBE, $Cu^{2+}$-ITCBE, $Fe^{2+}$-ITCBE and $Zn^{2+}$-ITCBE were diluted to a final concentration of 200 ng/mL with 0.01 M PBS. 100 μL of each was taken and dropwise added on a sample pad of the test strip, the test strip was put at a room temperature for reaction for 10 minutes, and the situations of disappearance of the line T of the test strip were observed to judge the specificity of the test strip. Results showed that the test strip had only a competitive reaction to an added $Hg^{2+}$-ITCBE complex, with a line T disappeared, while it had no obvious cross-reactivity to other ion chelates, indicating that the test strip had good specificity (FIG. 13A-13B).

2) Determination of Specificity of Gold-Nanoflower Chromatographic Strip

Figure 14A:
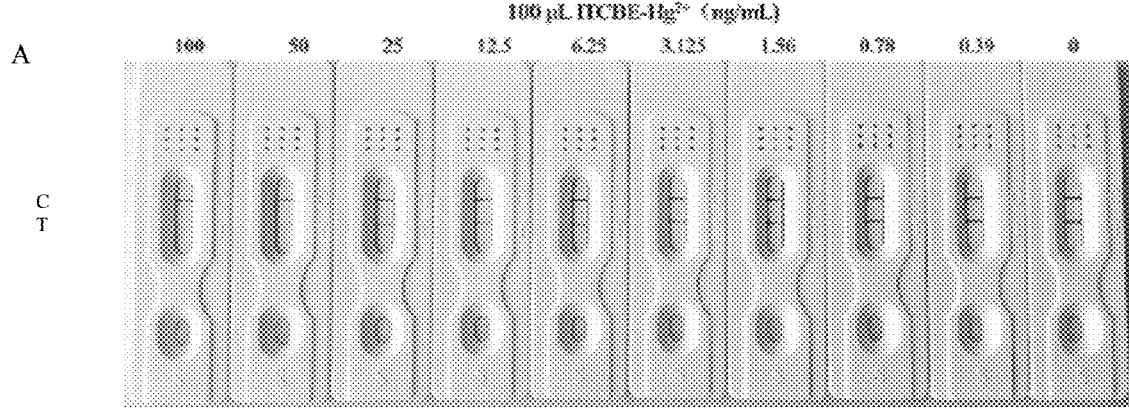
FIGS. 14A-14B show determination of sensitivity of the nanoflower immunochromatographic strip.
Figure 14B:
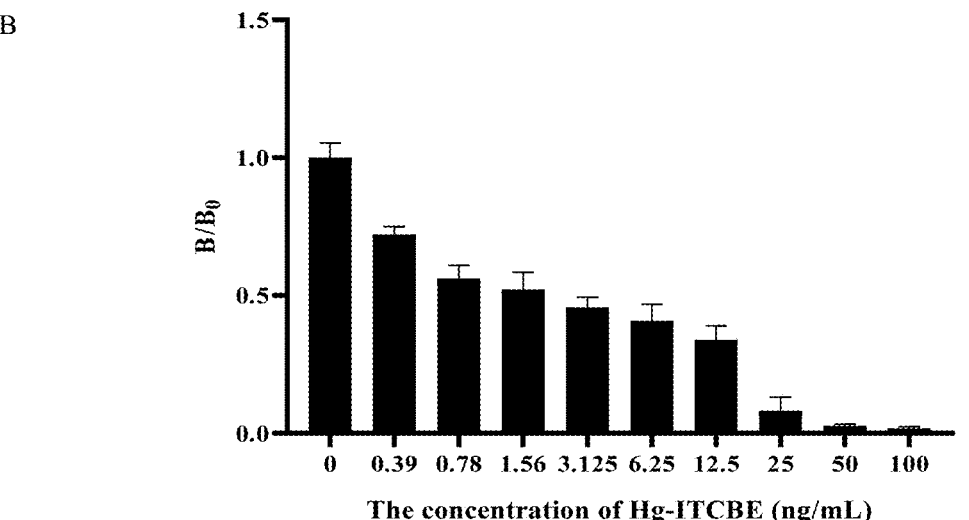

Streaking was conducted simultaneously on the NC membrane according to the above optimized dilution ratio of the best line C and the best line T, and the NC membrane after streaking was put in a 37° C. thermostatic incubator for drying for 15 minutes and then cut into strips; next, 3 μL of an immunoprobe was dropwise added on a probe joint pad, and a test strip was assembled well. $Hg^{2+}$-ITCBE was diluted to final concentrations of 50 ng/mL, 25 ng/mL, 12.5 ng/mL, 6.25 ng/mL, 3.125 ng/mL, 1.56 ng/mL, 0.78 ng/mL, 0.39 ng/mL and 0 ng/mL with 0.01 M PBS. Then, 100 µL of each was taken and dropwise added on a sample pad of the test strip, the test strip was put at a room temperature for reaction for 10 minutes, and the situations of disappearance of the line T of the test strip were observed to obtain a detection range of the test strip. Results showed that when the amount of $Hg^{2+}$-ITCBE added was 50 ng/mL, it could be observed that the line T disappeared obviously, indicating that an epitope of a gold-labeled antibody had been completely combined by a hapten $Hg^{2+}$-ITCBE in a sample, with the twofold dilution of concentration, it could be observed that the color of the line T was gradually darkened, under visible conditions, when a concentration was 0.78 ng/mL, there was an obvious change between the color of the line T and the color of a control strip, and when a concentration detected and displayed by an immune card reader was 0.39 ng/mL, an inhibition rate could reach 72% compared with the line T of a control group. Therefore, a visual detection limit of the immunochromatographic strip was 1.56 ng/mL, and a detection limit that the immune card reader can detect was 0.39 ng/mL (FIG. 14A-14B).

(6) Actual Sample Detection

Figure 15:
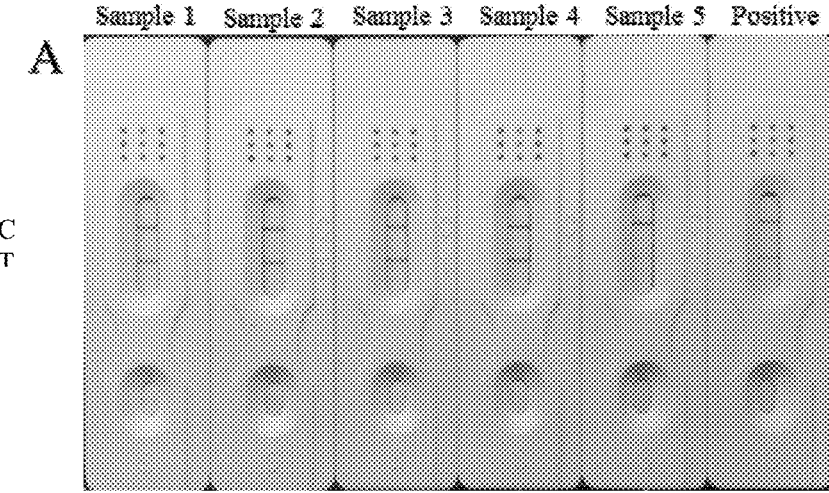
FIG. 15 shows detection of actual samples of the nanoflower immunochromatographic strip.

Streaking was conducted simultaneously on the NC membrane according to the above optimized dilution concentration of the best line C and the best line T, and the NC membrane after streaking was put in a 37° C. thermostatic incubator for drying for 15 minutes and then cut into strips. 3 µL of an immunoprobe was dropwise added on a probe joint pad, and a test strip was assembled well. Four major cereal crops were purchased randomly from supermarkets as detection objects, ground into powder with a mortar and subjected to a 0.5 mm test sample sieve, and sieved powder was collected. 1 mg of each of sieved rice, wheat, sweet potato and corn was taken respectively and put into four 2 mL centrifuge tubes, 1 mL of deionized water continued to be added to each of the four centrifuge tubes, in addition, 1 mL of a 200 ng/mL divalent mercury ion was taken as control, and excessive (400 ng) ITCBE was added into five solutions respectively and shaker-oscillated at 37° C. for 3 hours. After centrifugation at 1,000 r/min for 20 minutes, supernatants were collected separately and filtered with a 0.22 µm filter membrane, and then filtrates were taken for standby. Then, 100 µL of each of the rice, wheat, sweet potato and corn filtrates was taken and dropwise added on a sample pad of the test strip respectively, the test strip was put at a room temperature for reaction for 10 minutes, and the situations of disappearance of the line T of the test strip was observed. Results showed that by comparing the five samples with a control group (sample application with a PBS buffer solution), there was no obvious change in the color of line T of the four samples of rice, wheat, sweet potato and corn, indicating that there was no residual mercury ion in the samples; at the same time, compared with the control group, the line T of the test strip disappeared significantly (FIG. 15) in a sample with 200 ng of a standard substance of a mercury ion added, and this result was consistent with a result of atomic fluorescence spectrometry (Table 1), indicating that the test strip had good stability and could be applied to on-site detection of actual samples. It is of practical significance to detect the residue of heavy metal mercury ions in grains.

TABLE 1

| | Actual sample detection | |
| Samples | Detection results of Gold-nanoflowers immunochromatographic strip | AFS (µg/mL) |
| --- | --- | --- |
| Sample 1 | − | <0.003 |
| Sample 2 | − | <0.003 |
| Sample 3 | − | <0.003 |
| Sample 4 | − | <0.003 |
| Sample 5 | + | 0.13 |
| positive | − | <0.003 |

Note: a minimum detection limit of atomic fluorescence spectrometry is 0.003 µg/mL The foregoing descriptions are merely preferred embodiments of the present invention, and all equivalent changes and modifications made according to the scope of the present invention for patent application shall fall within the scope of the present invention.

What is claimed is:

1. A nanoflower immunochromatographic strip for detecting heavy metal mercury ions, wherein the nanoflower immunochromatographic strip comprises the following components: a plastic outer shell, a sample pad, an immunoprobe joint pad, a nitrocellulose (NC) membrane, and an absorbent pad; the immunoprobe joint pad is dropwise added with a gold nano-immunoprobe labeled with an anti-mercury-ion monoclonal antibody; the anti-mercury-ion monoclonal antibody is a monoclonal antibody secreted by a murine hybridoma cell strain 7A1; and the murine hybridoma cell strain 7A1 has been preserved in the China General Microbiological Culture Collection Center, with a preservation address at No. 3, Yard 1, Beichen West Road, Chaoyang District, Beijing, a preservation date on Nov. 23, 2021 and a preservation number of CGMCC No. 23879.

* * * * *